United States Patent
Englund et al.

(10) Patent No.: US 9,766,181 B2
(45) Date of Patent: Sep. 19, 2017

(54) WIDE-FIELD IMAGING USING NITROGEN VACANCIES

(71) Applicants: Dirk Robert Englund, Cambridge, MA (US); Matthew Edwin Trusheim, Cambridge, MA (US)

(72) Inventors: Dirk Robert Englund, Cambridge, MA (US); Matthew Edwin Trusheim, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 344 days.

(21) Appl. No.: 14/317,534

(22) Filed: Jun. 27, 2014

(65) Prior Publication Data

US 2015/0001422 A1    Jan. 1, 2015

Related U.S. Application Data

(60) Provisional application No. 61/840,852, filed on Jun. 28, 2013, provisional application No. 61/850,400, (Continued)

(51) Int. Cl.
*G01N 21/64* (2006.01)

(52) U.S. Cl.
CPC ..... *G01N 21/6458* (2013.01); *G01N 21/6486* (2013.01); *G01N 21/6489* (2013.01); *G01N 2021/6421* (2013.01)

(58) Field of Classification Search
CPC ....... G01N 2021/6421; G01N 21/6458; G01N 21/6486; G01N 21/6489
See application file for complete search history.

(56) References Cited

U.S. PATENT DOCUMENTS

| 7,778,296 B1 | 8/2010 | Vuckovic et al. |
| 2012/0019242 A1 | 1/2012 | Hollenberg et al. |

(Continued)

FOREIGN PATENT DOCUMENTS

| WO | 2009/073740 A2 | 6/2009 |
| WO | 2012/118944 A2 | 9/2012 |

(Continued)

OTHER PUBLICATIONS

Pham, Linh, "Magnetic Field Sensing with Nitrogen-Vacancy Color Centers in Diamond," Doctoral Dissertation, Harvard University, May 2013. Retrieved from internet [Mar. 30, 2016]; Retrieved from url:<http://nrs.harvard.edu/urn-3:HUL.InstRepos:11051173>.*

(Continued)

*Primary Examiner* — Yara B Green
(74) *Attorney, Agent, or Firm* — Cooley LLP

(57) ABSTRACT

Nitrogen vacancies in bulk diamonds and nanodiamonds can be used to sense temperature, pressure, electromagnetic fields, and pH. Unfortunately, conventional sensing techniques use gated detection and confocal imaging, limiting the measurement sensitivity and precluding wide-field imaging. Conversely, the present sensing techniques do not require gated detection or confocal imaging and can therefore be used to image temperature, pressure, electromagnetic fields, and pH over wide fields of view. In some cases, wide-field imaging supports spatial localization of the NVs to precisions at or below the diffraction limit. Moreover, the measurement range can extend over extremely wide dynamic range at very high sensitivity.

18 Claims, 14 Drawing Sheets

Related U.S. Application Data filed on Jul. 31, 2013, provisional application No. 61/860,410, filed on Jul. 31, 2013, provisional application No. 61/860,413, filed on Jul. 31, 2013.

(56) References Cited

U.S. PATENT DOCUMENTS

| | | | |
|---|---|---|---|
| 2013/0334170 A1 | 12/2013 | Englund et al. | |
| 2014/0072008 A1* | 3/2014 | Faraon | H01S 3/1681 372/45.01 |
| 2014/0094372 A1 | 4/2014 | Englund et al. | |
| 2014/0166904 A1* | 6/2014 | Walsworth | G01N 21/6489 250/459.1 |
| 2014/0191139 A1 | 7/2014 | Englund | |

FOREIGN PATENT DOCUMENTS

| | | |
|---|---|---|
| WO | 2013/040446 A1 | 3/2013 |
| WO | 2013/066446 A1 | 5/2013 |
| WO | 2013/188651 A1 | 12/2013 |
| WO | 2013/188732 A1 | 12/2013 |
| WO | 2014/099072 A1 | 6/2014 |

OTHER PUBLICATIONS

International Search Report and Written Opinion, dated Nov. 7, 2014 for PCT/US14/44618, filed Jun. 27, 2014, 13 pages.
Acosta, V. M. et al., "Electromagnetically Induced Transparency in a Diamond Spin Ensemble Enables All-Optical Electromagnetic Field Sensing," Physical Review Letters, vol. 110, May 22, 2013, pp. 1-6.
Aharonovich, Igor et al., "Diamond photonics," Nature Photonics, vol. 5, Jun. 30, 2011, pp. 397-405.
Arroyo-Camejo, Silvia et al., "Stimulated Emission Depletion Microscopy Resolves Individual Nitrogen Vacancy Centers in Diamond Nanocrystals," vol. 7, No. 12, Nov. 18, 2013, pp. 10912-10919.
Bartels, Bjorn et al. "Smooth optimal control with Floquet theory," arXiv preprint arXiv: 1205.5142v2 [quant-ph], Sep. 3, 2013, pp. 1-4.
Bar-Gill, N. et al., "Solid-state electronic spin coherence time approaching one second," Nature Communications, vol. 4, No. 1743, Apr. 23, 2013, pp. 1-6.
Bar-Gill, N. et al., "Suppression of spin-bath dynamics for improved coherence of multi-spin-qubit systems," Nature Communications, vol. 3, No. 858, May 22, 2012, pp. 1-6.
Chen, Edward H. et al., "Wide-Field Multispectral Super-Resolution Imaging Using Spin-Dependent Fluorescence in Nanodiamonds." Nano Letters, vol. 13, Apr. 2, 2013, pp. 2073-2077.
Doherty M. W. et al., "Theory of the ground-state spin of the NV$^-$ center in diamond," Physical Review B, vol. 85, May 3, 2012, pp. 1-5.
Doherty M.W. et al., "Electronic Properties and Metrology Applications of the Diamond NV$^-$ Center under Pressure," Physical Review Letters, vol. 112, 047601, Jan. 31, 2014, pp. 1-5.
Dolde, F. et al., "Electric-field sensing using single diamond spins," Nature Physics, vol. 7, Apr. 17, 2011, pp. 459-463.
Hegyi, Alex, et al., "Nanodiamond imaging: molecular imaging with optically-detected spin resonance of nitrogen-vacancy centers in nanodiamonds," Advances in Photonics of Quantum Computing, Memory, and Communication VI, Proc. of SPIE, vol. 8635, Feb. 6, 2013, pp. 1-8.
Hodges, J.S., et al., "Timekeeping with electron spin states in diamond," Physical Review A, vol. 87, Mar. 28, 2013, pp. 1-11.
Igarashi, Ryuji et al., "Real-Time Background-Free Selective Imaging of Fluorescent Nanodiamonds in Vivo," Nano Letters, vol. 12, Oct. 15, 2012, pp. 5726-5732.
Jensen K. et al., "Cavity-enhanced room-temperature magnetometry using absorption by nitrogen-vacancy centers in diamond," arXiv:1401.2438v1 [quant-ph], Jan. 10, 2014, pp. 1-5.
Jensen K. et al., Supplementary material to "Cavity-enhanced room-temperature magnetometry using absorption by nitrogen-vacancy centers in diamond," arXiv:1401.2438v1 [quant-ph], Jan. 10, 2014, pp. 1-3.
Kucsko, G., et al., "Nanometer scale quantum thermometry in a living cell" Nature, vol. 500, Aug. 1, 2013, pp. 54-58.
La Sage, D. et al.,"Efficient photon detection from color centers in a diamond optical waveguide," Physical Review B, vol. 85, 121202(R), Mar. 23, 2012, pp. 1-4.
Maletinsky, P. et al., "A robust scanning diamond sensor for nanoscale imaging with single nitrogen-vacancy centres," Nature Nanotechology, vol. 7, Apr. 15, 2012, pp. 320-324.
Mamin, H.J., "Nanoscale nuclear magnetic resonance with a nitrogen-vacancy spin sensor." Science vol. 339, Feb. 1, 2013, pp. 557-560.
Maze, J.R., "Nanoscale magnetic sensing with an individual electronic spin in diamond," Nature, vol. 455, Oct. 2, 2008, pp. 644-647.
McGuinness, L.P. et al, "Quantum measurement and orientation tracking of fluorescent nanodiamonds inside living cells," Nature Nanotechnology vol. 6, May 8, 2011, pp. 358-363.
Nusran, N.M., "High-dynamic-range magnetometry with a single electronic spin in diamond." Nature Nanotechnology vol. 7, Dec. 18, 2011, pp. 109-13.
Pham, L.M., et al.,"Magnetic field imaging with nitrogen-vacancy ensembles," New Journal of Physics, vol. 13, Apr. 28, 2011, No. 045021, pp. 1-13.
Rittweger, Eva et al., "STED microscopy reveals crystal colour centres with nanometric resolution," Nature Photonics, vol. 3, Feb. 22, 2009, pp. 144-147.
Schirhagl R. et al., "Nitrogen-Vacancy Centers in Diamond: Nanoscale Sensors for Physics and Biology," Annual Review of Physical Chemistry, vol. 65, Nov. 12, 2013, pp. 83-105.
Staudacher, T. et al., "Nuclear Magnetic Resonance Spectroscopy on a (5-Nanometer)3 Sample Volume," Science vol. 339, Feb. 1, 2013, pp. 561-563.
Steinert, S. et al., "Magnetic spin imaging under ambient conditions with sub-cellular resolution", Nature Comunications, vol. 4, No. 1607, Mar. 19, 2013, pp. 1-6.
Stoupin, S. et al., "Ultraprecise studies of the thermal expansion coefficient of diamond using back scattering x-ray diffraction," Physical Review B, vol. 83, Mar. 17, 2011, pp. 1-7.
Taylor, J.M., et al., "High-sensitivity diamond magnetometer with nanoscale resolution" Nature Physics, airXiv:0805.1367v1 [cond-mat.mes-hall], May 9, 2008, pp. 1-29.
Toyli, David M. et al., "Fluorescence thermometry enhanced by the quantum coherence of single spins in diamond" Proceedings of the National Academy of Sciences of the United States of America, vol. 110, No. 21, May 21, 2013. pp. 8417-8421.
Weidner, Donald J. et al., "Strength of Diamond," Science, vol. 266, Oct. 21, 1994, pp. 419-422.
Yang, X. et al., "STED imaging of Nitrogen-Vacancy Centers in Diamond," Ultrafast Imaging and Spectroscopy, Proc. of SPIE, vol. 8845, Aug. 25, 2013, pp. 1-5.
Zhang, W., et al. "Fiber Bragg grating pressure sensor with ultrahigh sensitivity and reduced temperature sensitivity," Optical Engineering, vol. 48, No. 2, 024402, Feb. 17, 2009, pp. 1-4.
Magnetic Field Sensing with Nitrogen-Vacancy Centers in Diamond, retrieved from web page https://dash.harvard.edu/handle/1/11051173?show=full on Jun. 29, 2016 at 2:03 PM, 3 pp.

\* cited by examiner

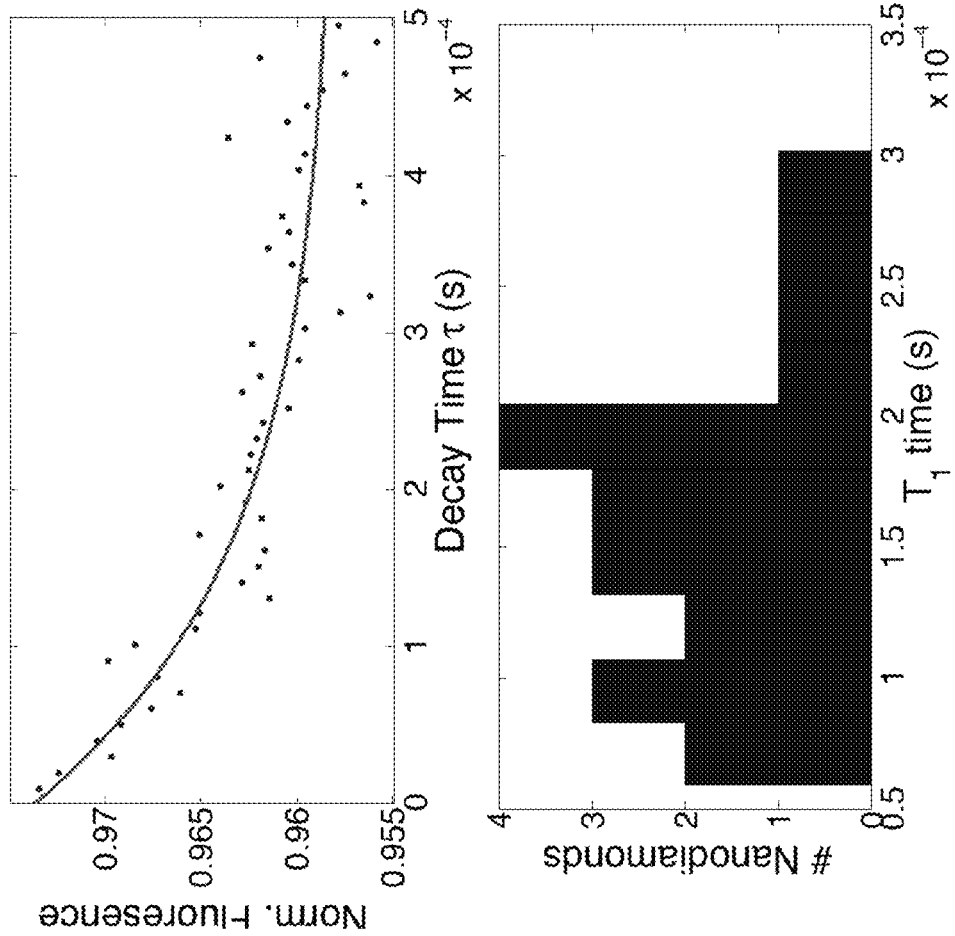
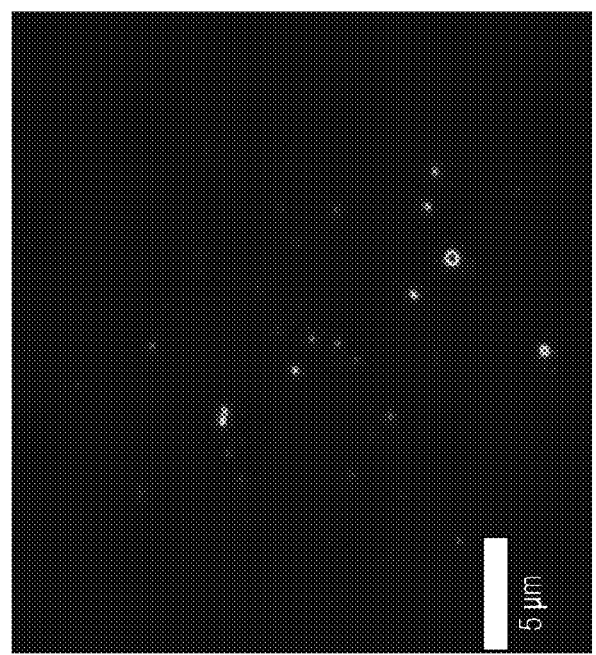
FIG. 13B
FIG. 13C
FIG. 13A

WIDE-FIELD IMAGING USING NITROGEN VACANCIES

CROSS-REFERENCE TO RELATED PATENT APPLICATIONS

This application claims priority, under 35 U.S.C. §119(e), from the following U.S. provisional applications, each of which is hereby incorporated herein by reference in its entirety:

U.S. Application No. 61/840,852, filed Jun. 28, 2013, and entitled "Pressure Sensor Using the Diamond Nitrogen Vacancy";

U.S. Application No. 61/860,400, filed Jul. 31, 2013, and entitled "Simple Method for Time-Resolved Optically Detected Magnetic Resonance Imaging across a Wide Field of View";

U.S. Application No. 61/860,410, filed Jul. 31, 2013, and entitled "Precision Optical Imaging of Arbitrary Electric Fields Using Spin States in Diamond"; and U.S. Application No. 61/860,413, filed Jul. 31, 2013, and entitled "Pressure Sensor Using the Diamond Nitrogen Vacancy."

GOVERNMENT SUPPORT

This invention was made with government support under contract number NNX13AE13H awarded by the NASA Goddard Space Flight Center. The government has certain rights in the invention.

BACKGROUND

The negatively charged nitrogen-vacancy center in diamond (NV) is an optically addressable room-temperature solid-state spin system with phase coherence times approaching one second. The NV center is electric-field sensitive through the Stark shift, which changes its electron spin energy levels in applied field. It has applications in many fields, including biology, where it is used as a fluorescent probe; quantum information, where it is used as a quantum bit; and sensing, where offers the ability to sense temperature, time, and electromagnetic fields with high precision.

For example, NV centers have been used to sense electric field with a spin echo technique. However, spin echo techniques involve both precise alignment of an external magnetic field with the NV orientation to achieve electric field sensitivity and a repetitive, phased-locked alternating-current (AC) electric field to achieve the highest resolution. (In general, alignment may be necessary for electric-sensitive spin echos, but not for spin echos.) As a result, these schemes are impractical for use with nanodiamonds which have random orientations in a tissue. Furthermore, to sense aperiodic electric fields, this scheme is limited to a non-dynamically decoupled phase acquisition time $T_2^*$ $T_2^*$ which is many orders of magnitude lower than what can be achieved using decoupling sequences. Since the magnetic field must be precisely aligned, fluctuations in field direction or off-axis magnetic noise can greatly diminish the sensitivity.

NV centers have also been used to sense DC magnetic fields using Ramsey interferometry, single-frequency AC magnetic fields using Hahn echo techniques, and general AC magnetic fields using repetitive dynamic decoupling sequences, such as the Carr Purcell Meiboom Gill (CPMG)-N dynamical decoupling sequence or the XY8·N dynamical decoupling sequence. These sequences rely on a differential phase acquired by different $S_z$ components of the spin ½ NV system, using a transition between the $m_s=0$ and a single $m_s=\pm 1$ state of the NV ground state spin triplet.

The transition between the ms=0 and a single ms=±1 state of the NV ground state spin triplet is pressure dependent through its relation to the strain of the diamond crystal. As such, measurement of the resonance frequency of this transition can give a readout of local pressure, with accuracy determined by the spin properties of the diamond as well as the specific method of spin probing. Two schemes use a π/4–π–/4 pulse sequence that addresses a double quantum transition between the ms=0 and both the degenerate $m_s=\pm 1$ and $m_s=-1$ levels. This sequence produces a signal that depends only on $S_z^2$, and therefore can sense local temperature or the frequency detuning of the driving microwave while providing immunity to other environmental effects, significantly including magnetic fields.

SUMMARY

The inventors have recognized the desire in quantum information and sensing applications to address the spins of multiple nitrogen vacancies (NVs) in parallel across a wide field of view, surpassing the limitations of serial addressing as performed in scanning confocal microscopy. Other demonstrations of wide-field addressing involve addressing dense ensembles of NVs, which does not allow for resolving individual NVs. As a result, it is generally not possible to estimate an NV's position with a resolution below the diffraction-limited resolution. Moreover, the pulse schemes used for addressing single NVs differ from those used in scanning confocal microscopy in that they involve the use of a long initialization pulse, during which the detectors are blocked or inactive.

Embodiments of the present invention include methods and systems for imaging color centers, including NVs, that address the shortcomings of other wide-field addressing schemes. Examples of these methods and systems enable wide-field imaging using single emitters and parallel control of spatially separated color centers (e.g., which may be used as qubits in a quantum information processor). In some examples, the system includes a light source, a microwave source, a wide-field imaging system for imaging radiation representative of an electric field, magnetic field, temperature, pressure, or strain applied to a plurality of color centers (e.g., NVs in bulk diamond or nanodiamonds), and, optionally, a processor operably coupled to the wide-field imaging system.

In operation, the light source irradiates the color centers with optical pulses (e.g., at a wavelength of 532 nm) so as to simultaneously excite one or more of the color centers from a first energy level to a second energy level and induce fluorescence emission from the color centers. (The emitted fluorescence represents the electric field, magnetic field, temperature, pressure, or strain applied to the color centers.) The microwave source applies a magnetic field to the color centers so as to manipulate an electron spin state of the first color center. And the wide-field imaging system images the fluorescence emitted by the color center(s) onto a detector array. The processor forms a representation of the electromagnetic field or the strain applied to the color centers based on the radiation imaged onto the detector array.

The color centers can be disposed on a surface of an inorganic material, such as a semiconductor, that is exposed to the electromagnetic field or the strain. The color centers can also disposed within organic tissue, including but not limited to neural tissue.

In some cases, the microwave source is configured to apply one or more microwave pulses to the color centers in an absence of any other magnetic field (e.g., a magnetic field applied with a permanent magnet or an electromagnet). The microwave source can also apply the magnetic field at a first orientation with respect to one color center and at a second orientation with respect to another color center so as to manipulate the electron spin states of both color centers.

Another example of the present invention is a system for imaging an electric field, magnetic field, temperature, pressure, or strain applied to a nanodiamond. The system can include a laser in optical communication with the nanodiamond, a wide-field imaging system in optical communication with the nanodiamond, a detector array disposed within an image plane of the nanodiamond, and a processor operably coupled to the detector array. In operation, the laser illuminates the nanodiamond with an optical pulse so as to simultaneously induce fluorescence emission of radiation from a nitrogen vacancy in the nanodiamond and excite the nitrogen vacancy in the nanodiamond from a first energy level to a second energy level. The wide-field imaging system images the fluorescence emitted by the nitrogen vacancy to a point in the image plane of the nanodiamond. The detector array senses the fluorescence emitted by the nitrogen vacancy. And the processor forms a representation of the electric field, magnetic field, temperature, pressure, or strain applied to the nanodiamond based at least in part on the radiation sensed by the detector array.

In some cases, the laser is configured to illuminate the nanodiamond with another optical pulse so as to simultaneously excite and induce fluorescence emission from another nitrogen vacancy (e.g., in another nanodiamond within the field of view). The wide-field imaging system is configured to image radiation emitted by another nitrogen vacancy within another nanodiamond to the image plane. And the system may also include a microwave source, in electromagnetic communication with the nanodiamond, to apply at least one microwave pulse to the nitrogen vacancy in the absence of any other magnetic field so as to manipulate an electron spin state of the first nitrogen vacancy.

Other color centers suitable for use with the embodiment disclosed herein include but are not limited to carbon vacancy defects replaced with extrinsic materials, such as silicon, sulfur, nickel, cobalt, etc. For example, a silicon atom may take the place of a missing carbon atom to form a negatively charged silicon vacancy color center. In other examples, carbon vacancy defects may be replaced by sulfur, nickel, or cobalt to form, respectively, sulfur, nickel, or cobalt vacancy color centers. In some of these embodiments, two carbon atoms may be missing and a single nickel atom may be situated in between the sites of the missing carbon atoms.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 13A-13C illustrate $T_1$ excited state lifetime (relaxometry) measurements in high-pressure, high-temperature (HPHT) nanodiamonds with a relatively high density of NVs (e.g., 100 ppm) and diameters of about 100 nm.

DETAILED DESCRIPTION

Figure 1B:
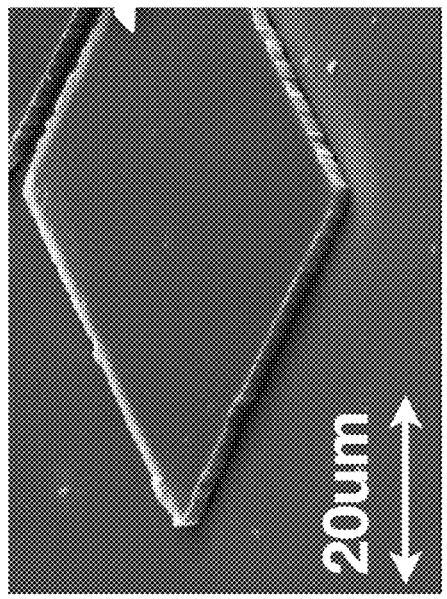
FIGS. 1A-1C illustrate diamonds that include nitrogen vacancies (NVs).
Figure 1C:
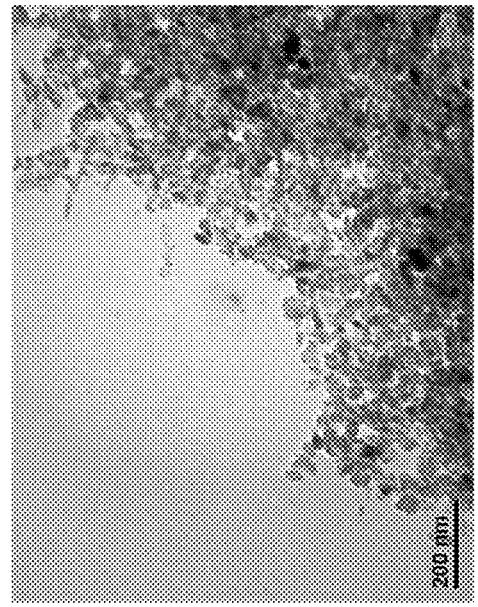

Embodiments of the present invention include methods and systems for time-resolved spin readout of nitrogen vacancies (NVs) and other color centers without fast gating or shuttering of the detector. One example includes time-resolved optically detected magnetic resonance (ODMR) imaging in NVs with an excitation and readout sequence in which the initialization and readout pulses are combined into a single pulse. This excitation and readout sequence, or measurement sequence, obviates the need for gating or shuttering the photodetector that detects the color centers' emissions during initialization.

Because these measurements do not involved gating or shuttering the photodetector, they can be performed with a standard detector, such as those in standard fluorescence microscopes. They do not necessarily involve modulating the fluorescence detection with gated cameras (e.g., intensified charge coupled devices (CCDs)), synchronized mechanical chopper wheels, electro-optic or acousto-optic shutters in the observation path. As a result, the measurements disclosed herein can occur faster than measurements involving optical chopping and other modulation techniques. In addition, the detector can average over a larger number of measurements, improving measurement sensitivity.

In addition, the combined readout/initialization techniques disclosed herein can be used to image NVs over a wide field of view (as opposed to other techniques, which often involve confocal imaging). When used with super-resolution imaging techniques, such as stochastic optical reconstruction microscopy (STORM), photo-activated localization microscopy (PALM), and the deterministic emitter switch microscopy techniques disclosed in WO/2013/188732 A1, which is incorporated herein by reference in its entirety, wide-field imaging can provide spatial resolution finer than the diffraction limit. Wide-field imaging reduces or eliminates averaging over inhomogeneous distribution of NV parameters and enables single-NV addressing (e.g., for qubit addressing and readout). Wide-field illumination can be provided by a continuous-wave laser that is modulated using a acousto-optic or electro-optic modulators. Alternatively, illumination can be provided by a gain-modulated laser diode.

The fluorescence emitted by the NVs varies with the pH, temperature, electromagnetic field(s), strain, and/or pressure applied to the NVs. As a results, NVs can be used to make very precise and very sensitive measurements of pressure, temperature, electromagnetic field(s), strain, and/or pressure over extremely wide dynamic ranges. For example, NV-containing diamonds (e.g., bulk diamonds and nanodiamonds) can be used to sense pressure in physical systems involving intense shock waves, compression, high-intensity sound, or explosions, such as fluids under compression in oil fields, oceans (e.g., for detecting tsunamis), explosions in atmosphere, etc. The ability to monitor huge static pressures, as well as obtain ultra-high precision, is useful in studies and applications in geology, oceanography, and atmospheric science, in addition to high pressure/high sensitivity flow sensing situations like those encountered in hydraulics and aerodynamics. In addition, NV-containing nanocrystalline diamond can be used as a biological labeling agent due to its cytocompatibility, non-bleaching fluorescence, and potential for spatial resolution below the diffraction limit.

Nitrogen Vacancy Energy Levels

Figure 1A:
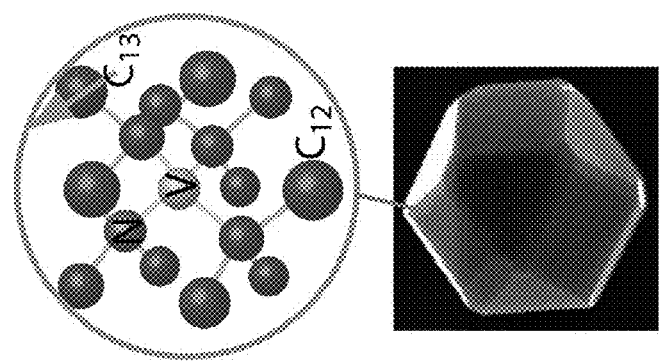

FIG. 1A shows a photograph of a diamond with a diagram of the nanodiamond's lattice of carbon ($C_{12}$ and $C_{13}$) with a nitrogen vacancy (NV) center. The NV center comprises a vacancy (V) adjacent to a substitutional nitrogen (N) in the diamond lattice. As well understood in the art, diamonds can be prepared with NV centers through appropriate nitrogen, helium and/or carbon implantation along with thermal and chemical treatment. These diamonds can be grown via chemical vapor deposition to form micron-scale crystals, as shown in FIG. 1B, or formed as nanodiamonds with diameters of less than 200 nm, as shown in FIG. 1B.

Figure 2B:
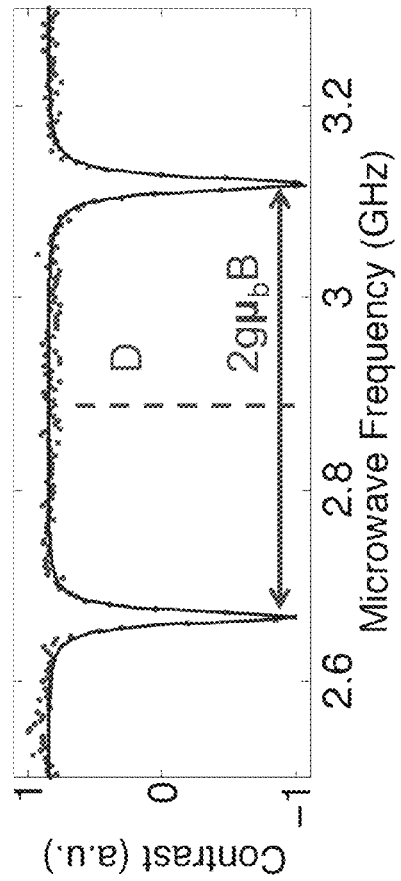
FIGS. 2A-2C illustrate energy level transitions in NVs due to pressure, strain, temperature, electric field, magnetic field, and nuclear spin manipulation.
Figure 2C:
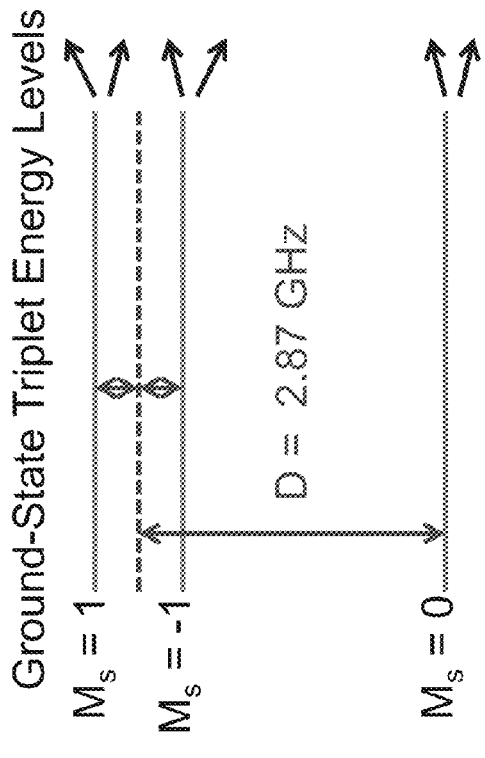
Figure 2A:
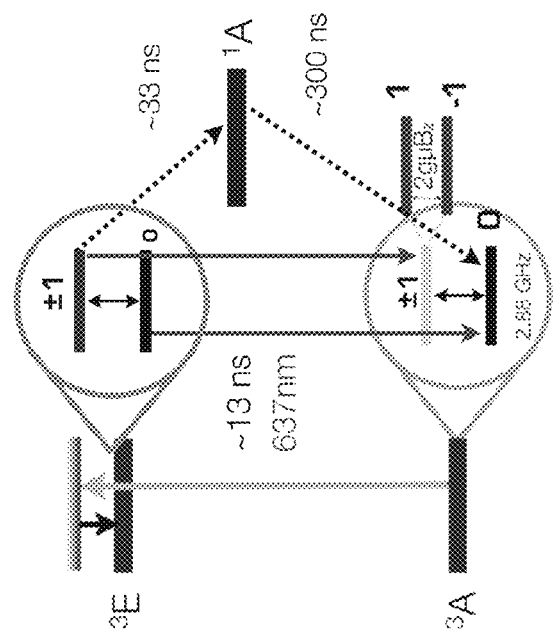

FIGS. 2A-2C illustrate the NV energy levels and resonant response. FIG. 2A shows the energy levels, including the lowest lying triplet ($^3E$, $^3A$) and singlet ($^1A$) orbital states of the NV. The NV can be excited from the $^3A$ triplet (the ground-state triplet) to the $^3E$ triplet by optical pumping at wavelength of about 637 nm to a higher energy followed by a nonradiative relaxation to the $^3E$ triplet state. FIG. 2B shows the ground-state triplet state energy levels in greater detail, with a ground state crystal field splitting $D_{gs}$=2.870 GHz. The splitting between the $m_s$=+1 and $m_s$=−1 spin states is proportional to the product of the Landé factor g, the Bohr magneton $\mu_b$, the magnetic field B. As shown in FIG. 2C, which is a plot of the resonances associated with the $m_s$=±1 spin states, the splitting is about 400 MHz and can be manipulated by excitation at microwave frequencies.

The Hamiltonian of an NV's electron ground state triplet can be described in the weak-field limit as:

$$H_{gs} = DS_z^2 + g\mu_B \vec{B} \vec{S} + \vec{S} \vec{A} \vec{I},$$

where D (also referred $D_{gs}$) is a parameter representing the crystal strain, temperature, and electric field applied to the NV; B is a parameter affected by magnetic field applied to the NV; and A is a parameter representing the NV's local nuclear spins. Because its Hamiltonian depends on the crystal strain, temperature, electric field, magnetic field, and nuclear spin, the NV can be used as a precision sensor of these quantities.

For instance, the D and B parameters can be determined through optically-detected magnetic resonance (ODMR), where laser light is used to prepare and read-out the spin state via spin-selective intersystem crossing processes, while resonant microwave excitation is used to manipulate the spin population. Many ODMR schemes have been demonstrated for use with the NV, including continuous-wave (CW) ODMR wherein microwaves and laser illumination are applied constantly, and pulsed ODMR techniques that include Ramsey-type sequences, Hahn echoes, and high-order repetitive dynamical decoupling. The pulsed measurements achieve maximal sensitivity in the determination of the NV energy levels by minimizing the resonance linewidth both by avoiding power broadening and by decoupling from sources of noise, achieving overall sensitivities that can be orders of magnitude lower than CW techniques.

Gated and Ungated Pulse Sequences for ODMR Measurements

Experimentally, room temperature pulsed NV ODMR comprises the repetitive application of pulse sequences. A single measurement may involve thousands of repetitions of an identical pulse sequence until enough photons have been collected to make a determination of the NV's spin state. Conventional pulse sequences, such as the measurement sequence 300 shown in FIG. 3A, generally involve initializing the NV spin to $m_s$=0 with a first optical initialization pulse 302a (e.g., at a wavelength of about 637 nm), manipulate the spin with a first sequence of microwave pulses 312a (e.g., a π/2-π-π/2 pulse sequence), and then read out the spin state with a first readout pulse 304a. The fluorescence from the initialization pulse is not indicative of any measurement result and is ignored, either by using fast detectors that can discriminate temporally between the initialization and readout pulses, or by shuttering a slow detector, e.g., with an optical chopper 322a that attenuates or blocks light propagating the sample to the photodetector.

Figure 3A:
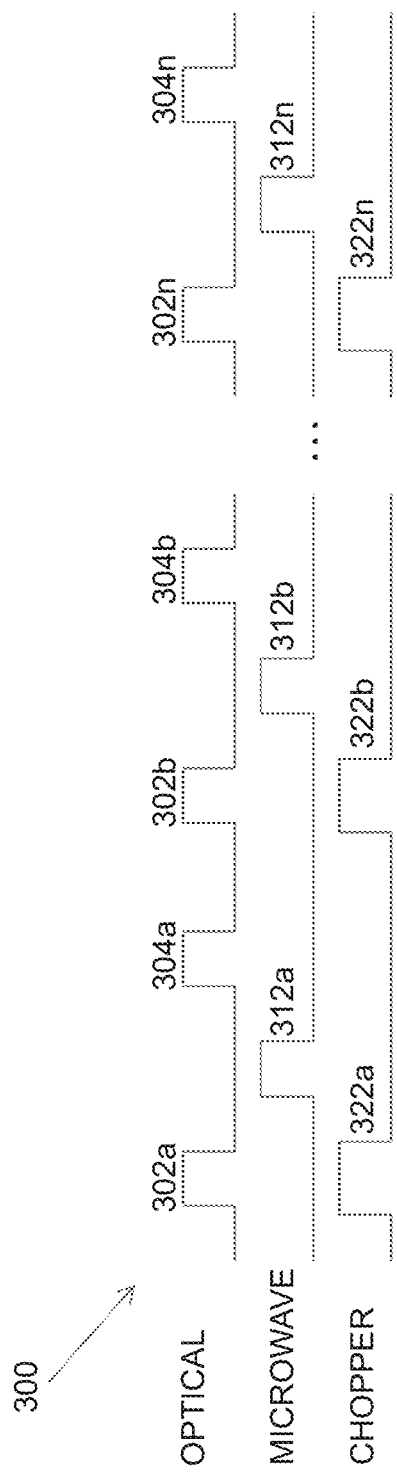
FIG. 3A illustrates a conventional gated sequence for measuring strain, temperature, electric field, magnetic field, and/or nuclear spin manipulation applied to an NV.

After the end of the first measurement cycle, the second measurement cycle occurs: a second optical initialization pulse 302b illuminates NVs in the sample while the optical chopper 322b blocks the photodiode, a second microwave pulse sequence 312b manipulates the NVs' spin states, and a second optical readout pulse 304b triggers fluorescence emission from the sample. The measurement sequence 300 may include as many measurement cycles as desired. However, the measurement sequence 300 shown in FIG. 3A is not directly applicable to wide-field localized sensing as both shutters and high-performance cameras are limited to rates much below the measurement repetition rate of up to 1 MHz, and therefore reduce the sensitivity of the measurement over a given length of time.

Figure 3B:
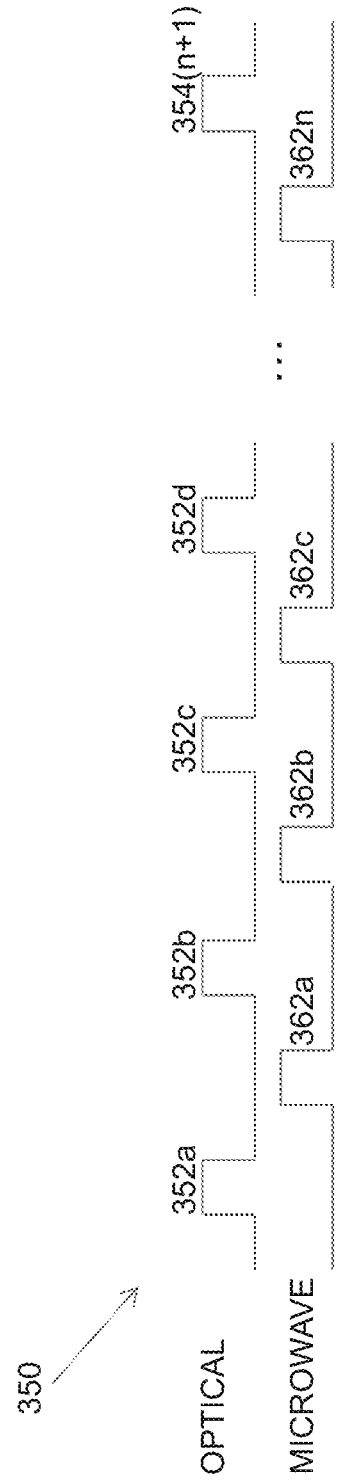
FIG. 3B illustrates a sequence for measuring for measuring pressure, strain, temperature, electric field, magnetic field, and/or nuclear spin manipulation applied to an NV.

FIG. 3B illustrates a measurement process 350 that uses successive optical pulses 352a, 352b, 352c, 352d . . . 352n (collectively, readout pulses 352) to re-initialize the spin state with high fidelity, thereby eliminating all of the initialization pulses except for the first initialization pulse with minimal loss in sensitivity. The optical pulses 352 serve to spin-polarize the NV. This creates a non-thermal state where the spin is out of thermal equilibrium (polarized). Each pulse 352 of optical illumination may excite all or substantially all of the color centers within the illuminated volume and also repolarizes those same color centers with each pulse. In the limit of a single color center, the emitted fluorescence is representative of the applied fields.

The measurement process 350 also includes microwave pulse sequences 362a, 362b, 362c, . . . 362n (collectively, microwave pulse sequences 362) that apply a magnetic field to the color centers so as to manipulate their spin states. Suitable microwave pulse sequences 362 include, but are not limited to Hahn Echo, Ramsey, Carr-Purcell-Meiboom-Gill (CPMG), XY, Thermal Echo, Rotary Echo, and Spin Locking sequences. Each microwave sequence 362 is applied within a period equal to the color center excited-state lifetime $T_1$ from polarization by the preceding optical pulse 352. And each microwave sequence 362 may span a duration of less than the color center coherence time $T_2$ for sensing purposes. (Other timing is also possible, depending on the desired sensitivity.)

Each color center addressed by the optical pulses 352 and microwave sequences 362 emits fluorescent light representative of the electric field, magnetic field, temperature, pressure, and/or strain applied to the color center. (Each color center may experience a different local electric field, magnetic field, temperature, pressure, and/or strain, so each color center may emit fluorescent light at a different wavelength.) A slow, high-sensitivity photodetector averages fluorescence emitted by NVs addressed by the optical pulses 352 and the microwave pulse sequences 362 over multiple cycles of the measurement sequence 350 (e.g., from 10 to 1,000,000 (e.g., 10,000) repetitions of the optical pulse 352 and the microwave sequence 362). Through this method, any pulsed ODMR sequence can be applied and read-out over a wide field without any specialized equipment, such as high-speed detectors and optical choppers.

Systems for Wide-Field Temperature, Pressure, and Field Measurements

Figure 4:
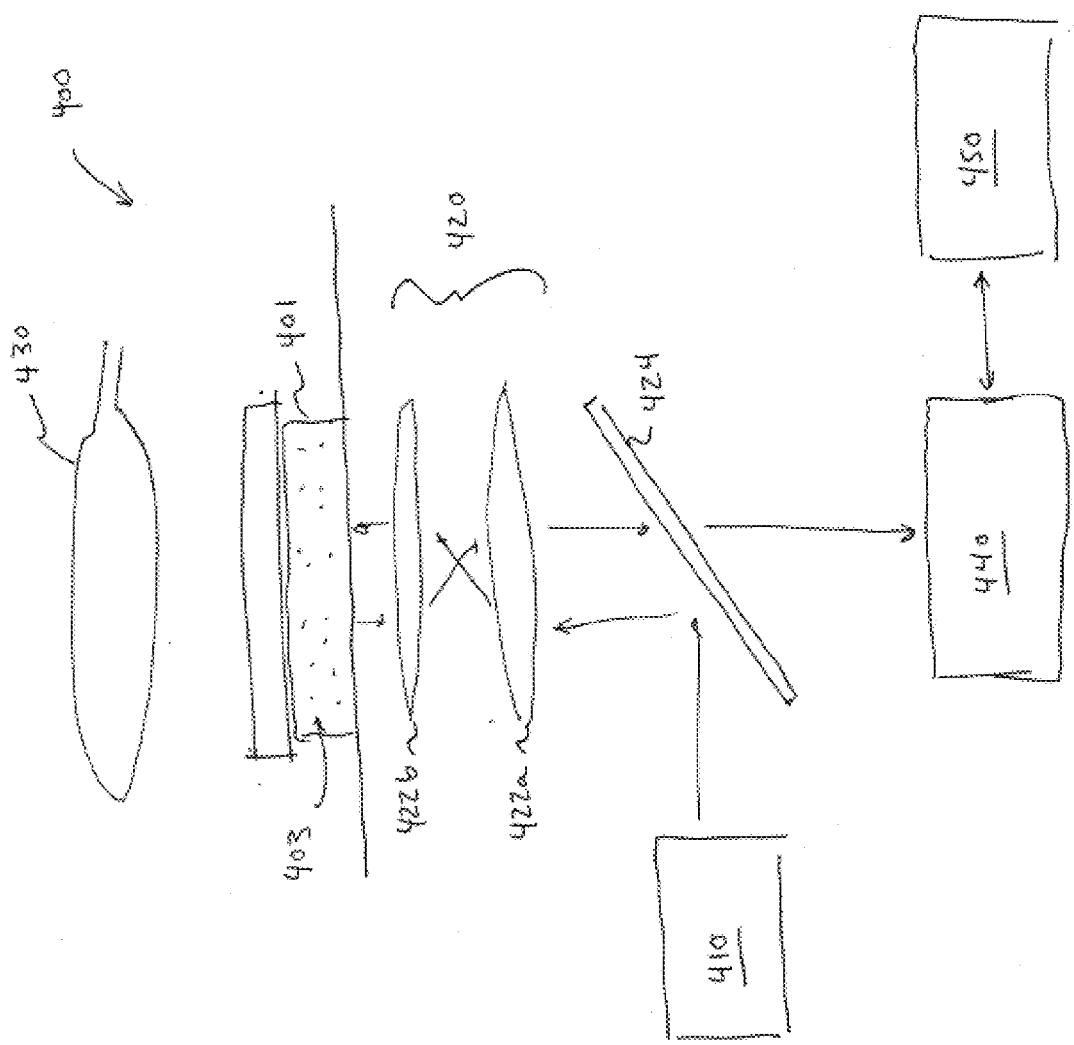
FIG. 4 is a diagram of a system for wide-field imaging of pressure, strain, temperature, electric field, magnetic field, and nuclear spin manipulation experienced by color centers distributed throughout a sample using the measurement sequence of FIG. 3B.

FIG. 4 illustrates a system 400 suitable for sensing temperature, pressure, electric fields, and magnetic fields applied to NVs and other color centers using the measurement sequence 350 of FIG. 3B. The system includes a light source, shown here as a laser 410, that illuminates a sample 401 comprising a plurality of color centers, shown here as NVs 403. For example, the sample 401 may comprise tissue that has been injected with NV-containing nanodiamonds. The sample 401 could also include an inorganic material, such as a semiconductor wafer, spin-coated with a layer of NV-containing nanodiamonds in solution. For example, the NVs 403 may be in a layer of diamond grown on the sample 401. The sample 401 could also contain other color centers in addition to or instead of NVs 401, including but not limited to carbon vacancy defects replaced with extrinsic materials, such as silicon, sulfur, nickel, cobalt, etc. For example, a silicon atom may take the place of a missing carbon atom to form a negatively charged silicon vacancy color center. In other examples, carbon vacancy defects may be replaced by sulfur, nickel, or cobalt to form, respectively, sulfur-, nickel-, or cobalt-vacancy color centers. In some cases, two carbon atoms may be missing and a single nickel atom may be situated in between the sites of the missing carbon atoms.

In operation, the laser 410 illuminates the NVs 403 with the series of optical pulses 352 shown in FIG. 3B via a wide-field imaging system 420, shown here as a microscope with a pair of lenses 422a and 422b (collectively, lenses 422) and a dichroic beamsplitter 424 that reflects the optical pulses 352 and transmits light at longer wavelengths. Suitable pulse wavelengths include but are not limited to 532 nm, 594 nm, and 637 nm; suitable pulse durations may range from about 300 ns to about 1000 ns; and suitable pulse shapes include but are not limited to square, Gaussian, Lorentzian, and other pulse shapes; and suitable peak pulse irradiances may range from about 1 µW to about 1 mW per square micron of illuminated area. If desired, the optical pulses 352 may be defocused so as to illuminate a large area (e.g., all or substantially all) of the sample 401 at once.

Between optical pulses, a microwave source, shown here as a loop antenna 430, drives the NVs with a sequence 362 of microwave pulses to apply a magnetic field to the NVs 403. The microwave field strengths may range from about 0.1 Gauss to about 100 Gauss at frequencies of about 2 GHz to about 4 GHz. Those of skill in the art will readily appreciate that the wide-field imaging system 420 may include more or fewer components, including but not limited to additional lenses, prisms, apertures, etc. The exact microwave pulse sequence 362 depends on the quantity—temperature, pressure, electric field, or magnetic field—that the system is measuring.

This microwave pulse sequence 362 manipulates the NVs' spin states, causing the NVs to emit fluorescent light at longer wavelength than the wavelength of the optical pulses 352. The lenses 422 image the light emitted by the NVs 403 to a detector array 440, such as a CCD array, in an image plane of the sample 401. The detector array 440 emits a photocurrent or other signal proportional to the detected radiation; a processor 450 coupled to the detector array 440 senses this radiation and uses it to produce an image or other representation of the temperature, pressure, electric field, or magnetic field applied to the NVs 403.

Figure 5:
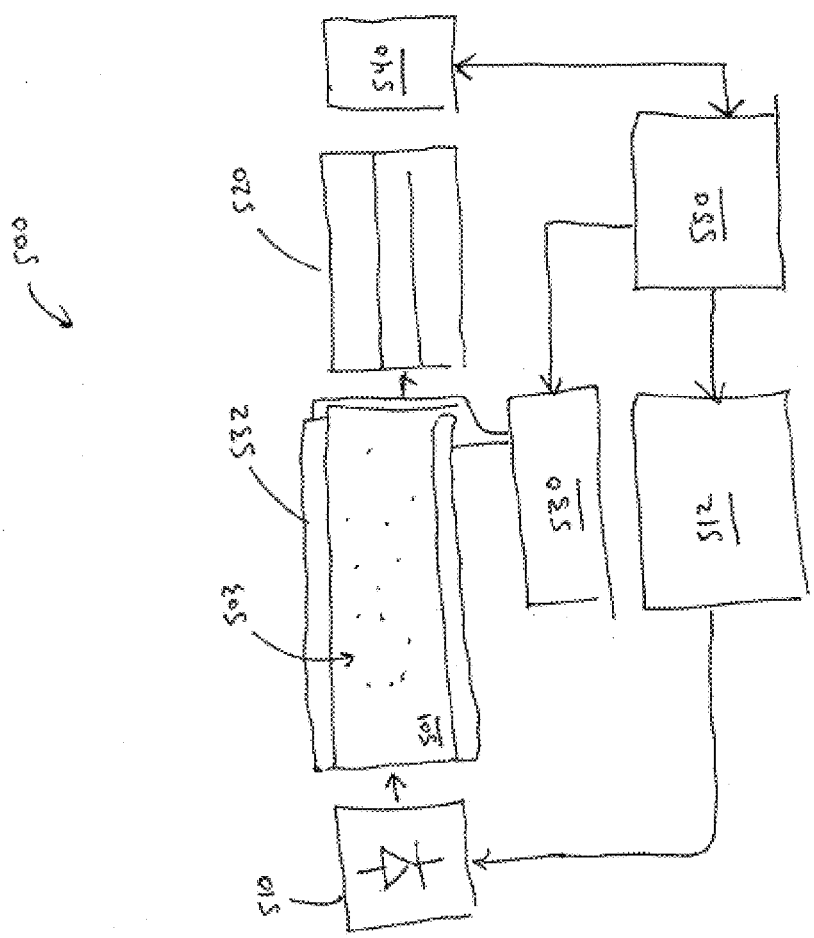
FIG. 5 is a diagram of an integrated system for imaging pressure, strain, temperature, electric field, magnetic field, and nuclear spin manipulation experienced applied to a color centers distributed throughout a sample using the measurement sequence of FIG. 3B.

FIG. 5 shows a integrated system 500 for measuring temperature, pressure, electric fields, and magnetic fields applied to NVs and other color centers using the measurement sequence 350 of FIG. 3B. In this integrated system 500, the light source, shown here as a laser diode 510, is butt coupled directly to a bulk diamond 501 that includes NVs 503 at a suitable density. Optical pulses from the laser diode 510 combined with microwave radiation from a microwave source, implemented here as a radio-frequency (RF) pulse generator 530 coupled to a microwave waveguide 532 disposed on the bulk diamond 501, cause the NVs 503 to emit fluorescent radiation whose amplitude and frequency depend on the applied microwave radiation and the temperature, pressure, electric fields, and magnetic fields applied to NVs 503. The fluorescent radiation is coupled into a waveguide 520 that transmits the fluorescent radiation to a photodetector 540, which generates a proportional photocurrent or other signal, and attenuates light at other wavelengths (including the wavelength of the laser diode 510).

A processor 550 coupled to the photodetector 540 receives the photocurrent and generates an indication representative of the temperature, pressure, electric fields, and magnetic fields applied to NVs 503. The processor 550 is also coupled to the RF pulse generator 530 and may also be used to select a different type of measurement, e.g., by varying the microwave pulse sequence emitted by the RF pulse generator 530. The processor 550 can also be coupled to a laser driver 512 that modulates the laser diode 510 so as to produce the optical pulses that initialize and readout the NVs 503.

Figure 6:
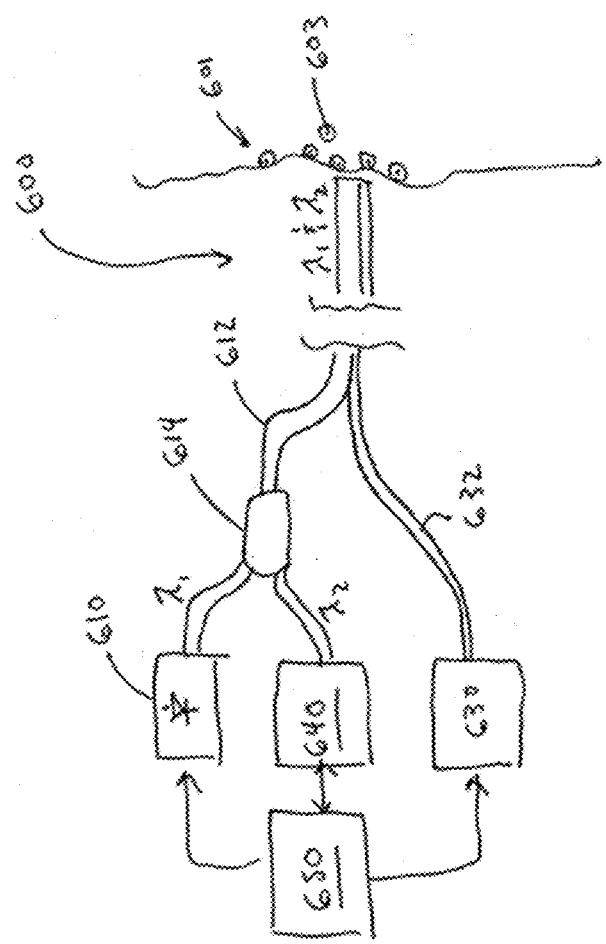
FIG. 6 is a diagram of a fiber probe for imaging pressure, strain, temperature, electric field, magnetic field, and nuclear spin manipulation experienced by color centers distributed throughout a sample using the measurement sequence of FIG. 3B.

FIG. 6 illustrates a probe 600 suitable for stimulating and measuring fluorescence emission from NVs 603 in nanodiamonds 601 deposited in or on tissue or other surfaces. An optical fiber 612 in the probe 600 guides pulses from a laser 610 to the tissue. These pulses initialize and excite the NVs 603 as described above with respect to FIG. 3B. (The probe 600 can also be used with other measurement sequences, including the sequence 300 shown in FIG. 3A.) The probe 600 also includes a microwave waveguide 632 that guide microwave pulses from a microwave source 630 to the NVs 603. The microwave pulses manipulate the NVs' spin states, causing the NVs 603 to fluoresce upon application of subsequent optical pulses. (As described in greater detail below, the microwave pulses may be selected based on the desired measurement.)

The optical fiber 612 guides a portion of the fluorescent light emitted by the NVs back to a photodetector 640 via wavelength-division multiplexing filter 614. The photodetector 640 emits a photocurrent or other signal proportional to the detected radiation; a processor 650 coupled to the photodetector 640 senses this radiation and uses it to produce an image or other representation of the temperature, pressure, electric field, or magnetic field applied to the NVs 603.

Pressure Sensing in Nitrogen Vacancies

Diamond is one of the hardest materials discovered and is widely used in anvils for high-pressure experiments. Diamond has been shown to not experience any deformation at pressures up to 10 GPa and temperatures up to 1000 degrees Celsius. The strain relation across this pressure range is linear, which indicates that even higher pressures might be obtainable and that modeling the resonance shift as a linear function is a reasonable approximation.

The systems and pulse sequences described above can be used to measure pressure (and temperature) applied to NV-containing diamond(s) across a dynamic range that extends from ambient pressure to 10 Gpa. Moreover, the sensitivity of these pressure sensors can be finer than about $10^{-2}$ Pa/√Hz across the entire dynamic range. As explained with respect to FIGS. 2A-2C, the NV has a ground state spin triplet whose Hamiltonian includes a parameter D that varies with the temperature of and the pressure applied to the NV. The parameter D has a temperature dependence of 77 kHz $K^{-1}$, which is the basis for the NV temperature sensor.

Temperature couples to the NV spin levels through the thermal expansion of the diamond lattice, whose expansion or contraction changes the effective internal electric field of the NV. Shifting this internal field by other methods, e.g., by inducing axial strain, produces the same effect. The thermal expansion coefficient of diamond at room temperature is proportional to $9 \times 10^6$ $K^1$, while the Young's modulus of diamond is about E=1050 GPa. Assuming that temperature produces its strain shift of $\delta\omega$=77 kHz $K^{-1}$ through induced strain, an applied pressure produces a frequency shift per unit pressure of $\Delta\Omega = \delta\omega/\alpha E = 8.1 \times 10^{-3}$ Hz $Pa^{-1}$.

The precision with which a frequency change can be sensed is given by the Allan deviation of the diamond sensor used. Any resonance sequence that is sensitive to $D_{gs}$ could be used to sense pressure using a NV sensor, including continuous wave electron spin resonance sequences, Ramsey sequences, and electromagnetically-induced transparency schemes. For enable optimal performance, some sequences can isolate this term from environmental effects such as electric and magnetic fields. For example, a π/4–π–π/4 pulse sequence, also known as the spin-1 protocol, yields a signal proportional to sin φ, where φ=(Dω)T, ω is the angular frequency, and T is the temperature. As explained in J. S. Hodges et al., Physical Review A 87, 032118 (2013), which is incorporated herein by reference in its entirety, the Allan deviation can be expressed as:

$$\left(\frac{\delta\omega}{\omega_0}\right)_{M'} = \frac{\xi}{D_{gs}\sqrt{T\tau N}}.$$

For reasonable values of readout efficiency ξ, coherence time τ, and number of color centers (NVs) N (e.g., ξ=0.3, τ=1 ms, and N=$10^6$) this gives a theoretical fractional frequency deviation of $2 \times 10^{-13}$ 1/√Hz. At this fractional frequency deviation, the frequency detection threshold is about $6 \times 10^{-3}$ Hz/√Hz, which corresponds to a minimum detectable pressure differential of $10^{-2}$ Pa/√Hz. Other parameters that can affect the minimum detectable pressure differential include the NV spin coherence time $T_2$, collection signal-to-noise ratio (SNR), number of addressable emitters, and homogeneity of the sample in terms of spin resonance response. Experimental demonstrations have shown an NV temperature sensitivity of $9 \times 10^{-3}$ mK/√Hz, which corresponds to a pressure sensitivity of about $10^4$ Pa/√Hz.

As explained above, NV centers occur naturally in diamond and can also be induced through various implantation and thermal processes to achieve control over density and coherence properties. NV nuclear spin can measured via a sequence of initialization, manipulation, and readout—for example, the ungated sequence with combination readout/re-initialization pulses shown in FIG. 3B. Spin initialization is generally achieved with high efficiency via optical pumping, though large magnetic fields could also be used. Manipulation between the relevant spin states can be achieved with the application of microwaves, optically via Raman processes, or magnetically with a field bias near a level anti-crossing. Readout is optical, with laser excitation at a wavelength less than 638 nm and fluorescence detection in the range from 637-800 nm.

One implementation of the diamond pressure sensor involves the following procedure. A high-quality CVD diamond is prepared with a large total number of NV centers through appropriate nitrogen, helium and/or carbon implantation along with thermal and chemical treatment. (The color center can limit the spin coherence, so in many cases the diamond should have a low color center density but a large number of color centers.) The diamond is then disposed in, on, or near the area where pressure or strain is to be measured. Resonant microwave excitation is provided in the near field via on-chip waveguides or in the far field through an external cavity or frequency horn as described above. High-isolation switches and high-fidelity amplifiers modulate and amplify, respectively, microwave excitation from a microwave signal generator. Laser excitation at a wavelength of 532 nm is coupled onto the diamond chip through fiber optics, while the fluorescence is collected by a photodiode at high efficiency on the edge of the diamond through the use of mirror coatings on the non-collection surfaces of the chip. The laser excitation can be switched via free-space acousto-optic or fiber-coupled electro-optic modulators. A computer-controlled interface coupled to the laser, the optical modulator, the microwave signal generator, and the photodiode synchronizes the optical and microwave excitation and output collection.

Precision Optical Imaging of Arbitrary Electric Fields

The sensors and measurement sequences disclosed herein can used be used with a spin-1 protocol to detect electric fields. As understood by those of skill in the art, the spin-1 protocol comprises a $\pi/4$-$\pi$-$\pi/4$ microwave pulse sequence that creates a coherence between $m_s=0$ and a superposition of $m_s=1$ and $m_s=-1$, both states which have no magnetic moment. In this protocol, the NV's Hamiltonian is sensitive only to the D parameter, which is sensitive to electric field. This technique is insensitive to magnetic fields in both alignment and magnitude, to first order. In addition, it makes use of the fully decoupled $T_2$ time of the NV spin to read an aperiodic electric field, which allows it to scale to measure electric field at different sensitivities. In addition, this technique offers electric field sensitivity that is fine enough to detect a neuronal action potential change at millisecond-scale time resolution. Furthermore, the sensitivity can be made finer by addressing additional NVs. The technique is compatible with wide-field readout and super-resolution imaging, which allows the recording of electric field with sub-diffraction resolution across ensembles of neurons.

An example electric-field imaging system can be used to address multiple NVs simultaneously, despite the NVs' different orientations relative to microwave drive axis. More specifically, an example electric-field imaging system may include a microwave source that emits multiple microwave frequency components to manipulate the electron spin so as to achieve tolerance to both detuning of the resonance frequency and differing drive field magnitudes (different Rabi frequencies across different NVs). This imaging technique is compatible with standard fluorescence microscopes and cameras and with two-photon microscopy. It does not require an external magnetic field, and its use is not restricted to life sciences—other suitable applications include semiconductor measurements, material science, etc.

As explained above, the NV has a ground state spin triplet described by the Hamiltonian:

$$H_{gs}=DS_z^2+g\mu_B\vec{B}\vec{S}+\vec{S}A\vec{I},$$

which can be rewritten as:

$$H_{gs}=(D_{gs}+d_{\parallel}s_z)DS_z^2+g\mu_B\vec{B}\vec{S}+\vec{S}A\vec{I},$$

where $D_{gs}$ represents the ground state crystal field splitting (2.870 GHz), $d_{\parallel}$ represents the ground state electric dipole moment along the $C_{3v}$ symmetry axis of the NV, and $\sigma_z$ represents the electric field vector in the z direction. To sense an electric field, the sensors disclosed herein measure changes in the $d_{\parallel}$ parameter, which has a value of 0.35 Hz cm $V^{-1}$. For reasonable values of readout efficiency $\xi$, coherence time $\tau$, and number of color centers (NVs) N, this gives a theoretical fractional frequency deviation of $(10^{-10}/\sqrt{N})$ $1/\sqrt{Hz}$. At this fractional frequency deviation, the frequency detection threshold is about 10 Hz/$\sqrt{Hz}$ for a single NV, which corresponds to a possible electric field sensitivity of about 30 V cm$^{-1}$ Hz$^{-1/2}$. Parameters that affect the electric field sensitivity include the NV spin coherence time, the collection SNR, the number of addressable emitters, and the homogeneity of the sample in terms of spin resonance response. An experimental demonstration shows a temperature sensitivity of $2.5\times10^{-2}$ K/$\sqrt{Hz}$, which corresponds to an electric field sensitivity of about $5\times10^3$ V cm$^{-1}$ Hz$^{-1/2}$. A neural action potential has a field of roughly $1.4\times10^5$ V/cm, which can be resolved with this experimentally demonstrated sensitivity in 1.4 ms.

Experimental Demonstration

Figure 7:
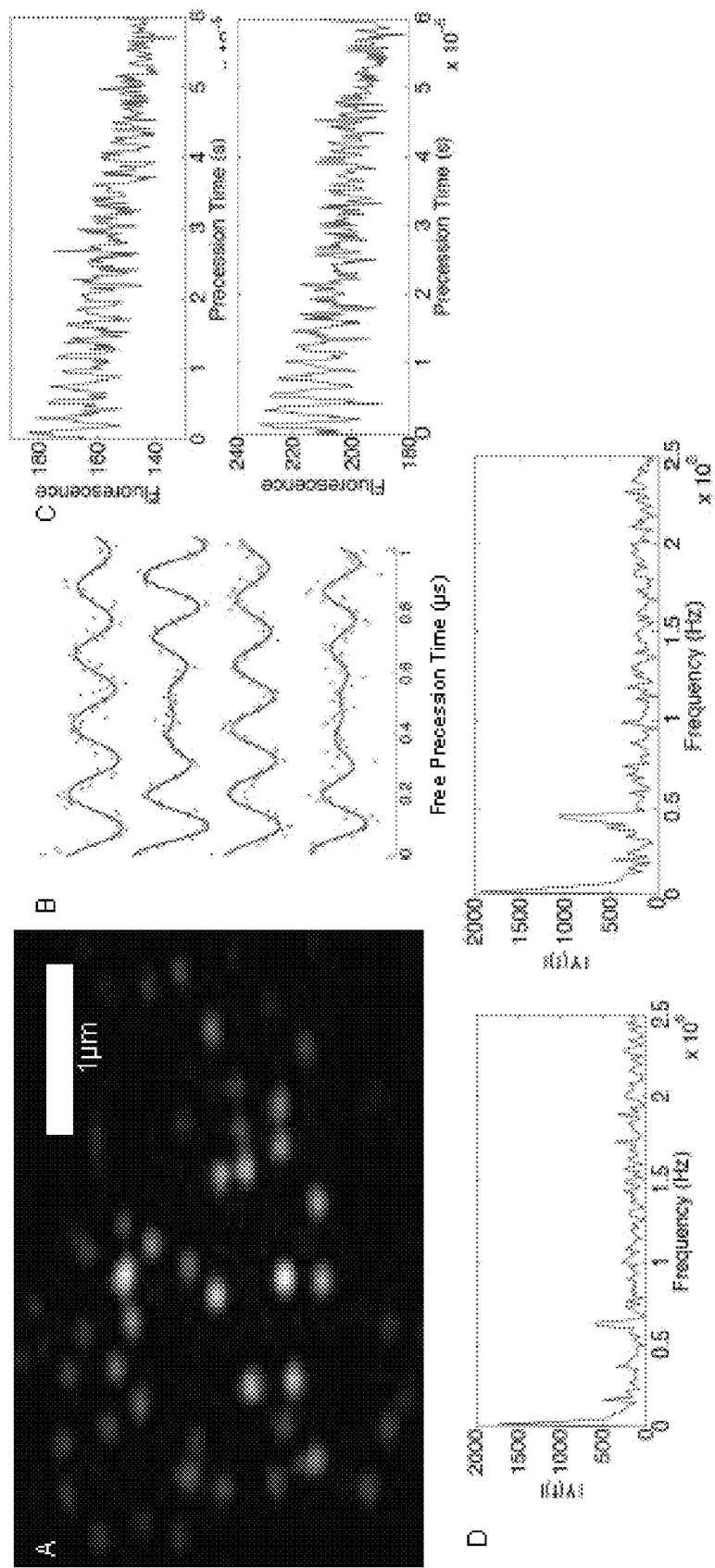
FIGS. 7A-7D illustrate wide-field fluorescence emission from NVs in bulk diamond.

FIGS. 7A-7D illustrate wide-field fluorescence imaging in bulk diamond. FIG. 7A is a wide-field fluorescence image of NVs in a bulk diamond. FIG. 7B is a plot of the normalized fluorescence versus for four NVs; it shows simultaneous Rabi oscillations being driven across the sample. FIG. 7C shows plots of fluorescence versus precession time for a pair of NVs subject to a spin-1 thermometry sequence executed in parallel. The two NVs are dynamically decoupled to a coherence time $T_2$>20 ms. FIG. 7D includes plots of the Fourier transform of thermometry signals shown in FIG. 7C; it reveals different oscillation frequencies, indicative of differing local strain experience by the NVs. The different oscillation frequencies correspond to different values of the $d_{\parallel}$ parameter, which in turn indicates a different strain or temperature. In this case, the different oscillation frequencies likely represent different strains rather than different temperatures as the NVs are at thermal equilibrium.

The NV-enabled temperature sensing protocol illustrated in FIGS. 7A-7D leverages the spin-1 nature of the NV to enable nanoscale thermometry. This protocol is sensitive to the energy difference between the $m_s=-1$ and $m_s=0$ sublevels of the NV electron ground state spin triplet, which in turn varies with temperature as well as local crystal strain. Using this scheme in parallel across a bulk diamond, hundreds of NVs can be monitored simultaneously, allowing for rapid data sampling across a wide field of view. Experimental results show coherence times in excess of 50 ms and calculated temperature sensitivities of <100 mK. In addition, this technique reveals the internal strain of the diamond with nanoscale spatial precision.

This technique can also be used to sense electromagnetic fields, strain, and/or temperature across a large field of view. Specifically, multi-pulse electric and magnetic field sensing measurements can be performed in parallel across large numbers of individually resolved NVs. Numerically optimized microwave control can enhance the fidelity of spin operations across inhomogeneous qubits. This wide-field technique sets the stage for the use of localized NVs as sensors for mapping quantities of interest in parallel.

Figure 8B:
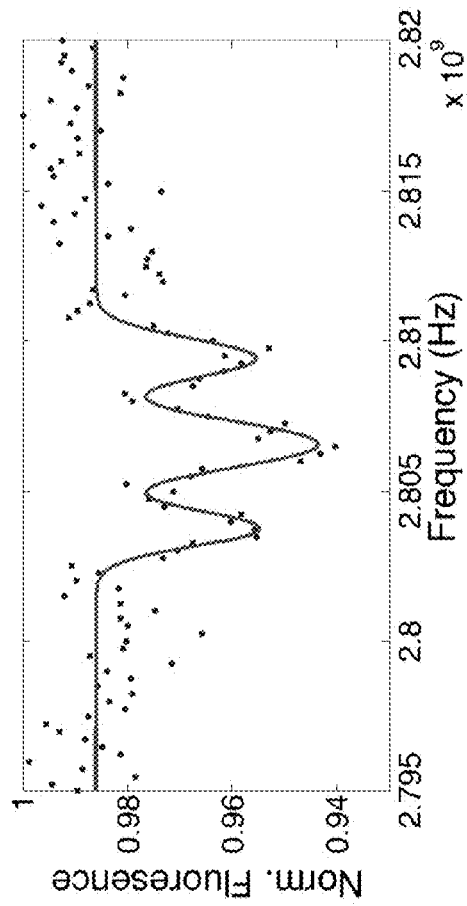
FIGS. 8A-8C illustrate pulsed frequency sweep measurements of a CVD diamond with a relatively low density of NVs (e.g., 5 ppb).
Figure 8C:
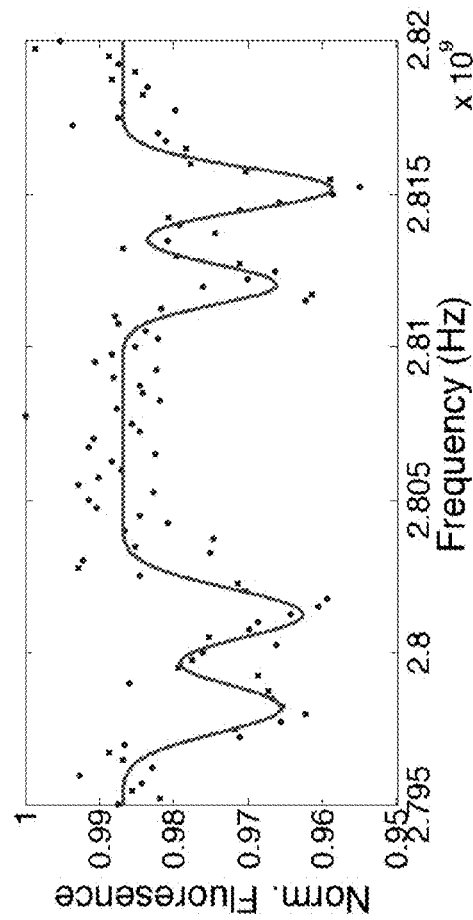
Figure 8A:
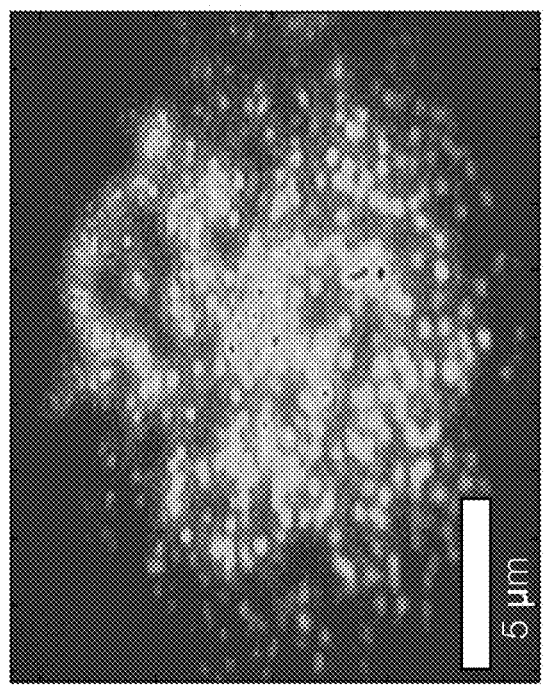

FIGS. 8A-8C illustrate pulsed frequency sweep measurements of a CVD diamond with a relatively low density of NVs (e.g., 5 ppb). These NVs were created by a dose of $5\times10^8$ nitrogen atoms per square centimeter imparted on the sample with an energy of 6 keV. The diamond is illuminated with the optical pulses of FIG. 3B and a microwave pulse sequence that includes a chirp (i.e., a swept-frequency microwave pulse). FIG. 8A is a wide-field image of fluorescence emitted by the NVs. FIGS. 8B and 8C are plots of normalized fluorescence versus microwave frequency for NVs. The frequency sweep reveals the A parameter of the NV center, showing coupling to different nuclear spins (e.g., carbon 13, nitrogen 14, and nitrogen 15), which is useful for quantum information purposes. For example, because the nuclear spins have long phase lifetimes, they can be used to store quantum states.

Figures 9A, 9B, 9C:
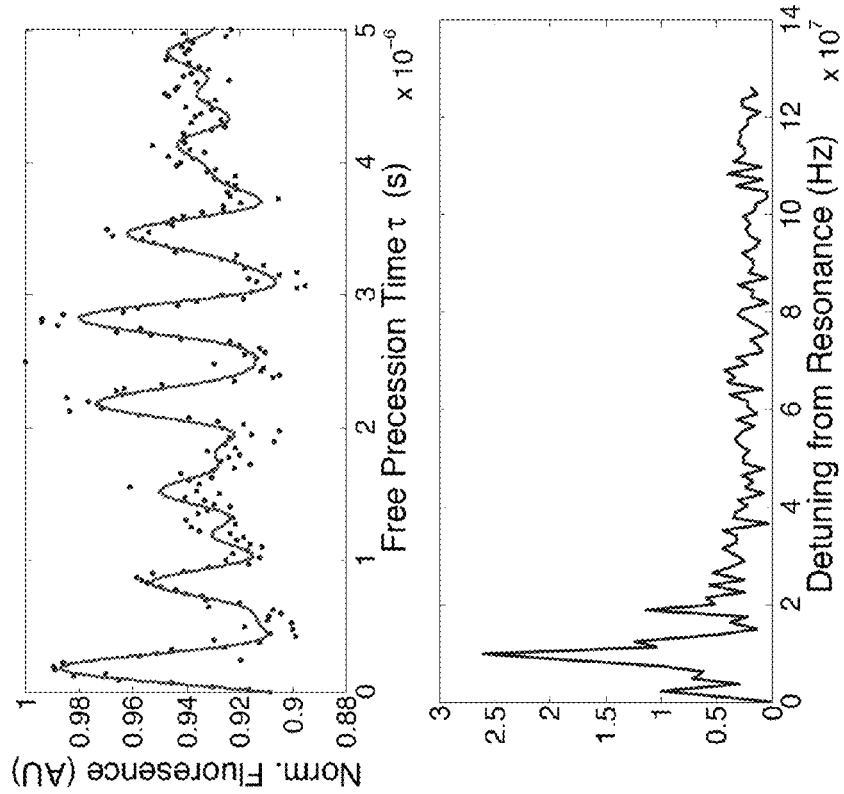
FIGS. 9A-9C illustrate Ramsey measurements of a CVD diamond with a relatively low density of NVs (e.g., 5 ppb).

FIGS. 9A-9C illustrate Ramsey measurements of a CVD diamond with a relatively low density of NVs (e.g., 5 ppb). These NVs were created by a dose of $5 \times 10^8$ nitrogen atoms per square centimeter imparted on the sample with an energy of 6 keV. The diamond is illuminated with the optical pulses of FIG. 3B and a microwave pulse sequence that includes a Ramsey sequence (i.e., a π/2 pulse followed by another π/2 pulse after a free precession time Δt). FIG. 9A is a wide-field image of fluorescence emitted by the NVs. FIGS. 9B and 9C are plots of normalized fluorescence versus the free precession time and the detuning from resonance, respectively. Ramsey pulse sequences have applications in precision direct-current (DC) magnetometry.

Figure 10B:
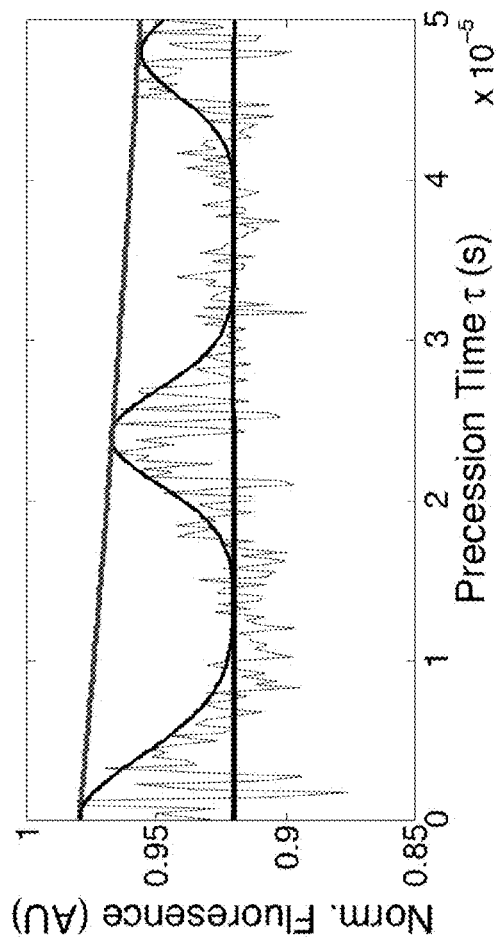
FIGS. 10A and 10B illustrate Hahn echo measurements of the diamond of FIGS. 8A-8C and 9A-9C.
Figure 10A:
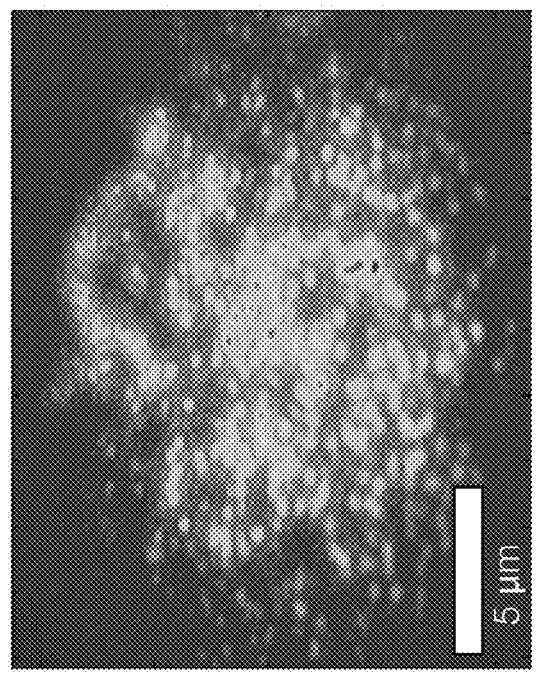

FIGS. 10A and 10B illustrate Hahn echo measurements of the diamond of FIGS. 8A-8C and 9A-9C. The diamond is illuminated with the optical pulses of FIG. 3B and a microwave pulse sequence that includes a Hahn echo sequence (i.e., a π/2 pulse, a first free precession time Δt, a π pulse, a second free precession time Δt, and another π/2 pulse). FIG. 10A is a wide-field image of fluorescence emitted by the NVs. FIG. 10B is a plot of normalized fluorescence versus the free precession time. FIG. 10B shows that the coherence time is about $T_2$=200 µs. Hahn echo pulse sequences have applications in precision alternating-current (AC) magnetometry and coherence characterization.

Figure 11A:
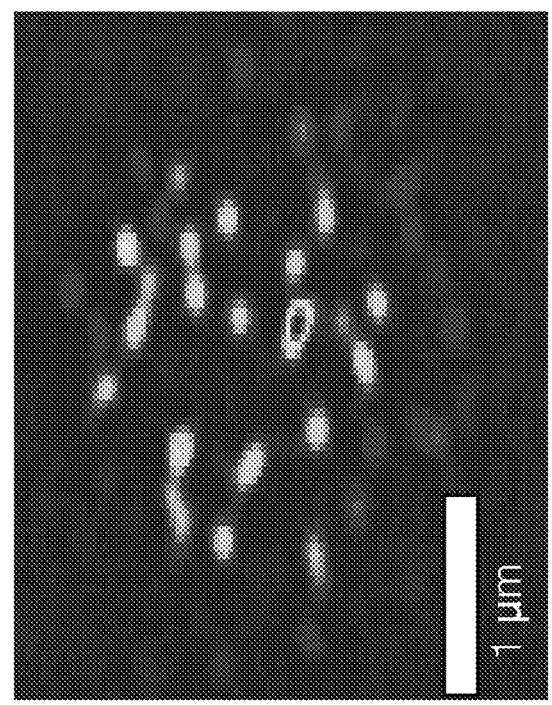
FIGS. 11A-11C illustrate thermal echo measurements of a CVD diamond with a relatively low density of NVs (e.g., 5 ppb).
Figure 11B:
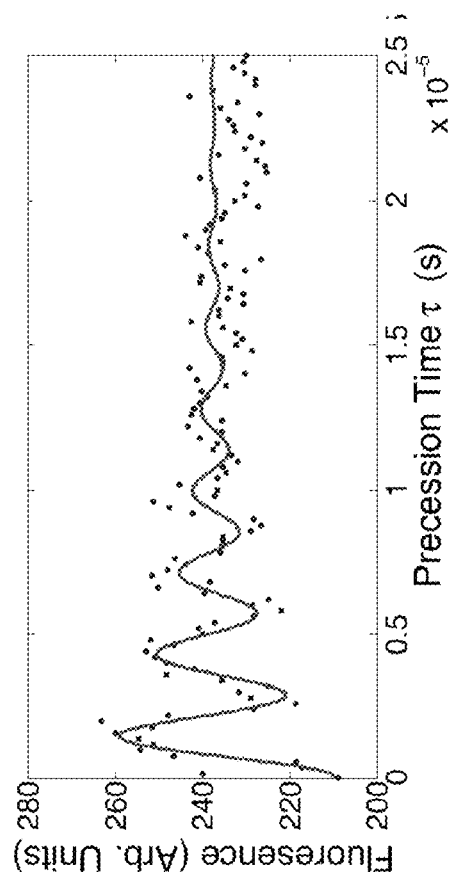
Figure 11C:
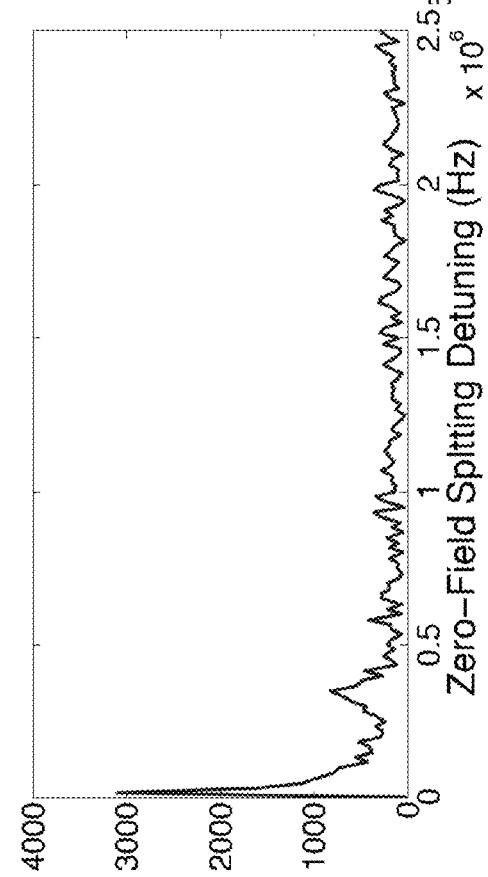

FIGS. 11A-11C illustrate thermal echo measurements of a CVD diamond with a relatively low density of NVs (e.g., 5 ppb). Thermal echo sequences are a specific sequence used for thermometry; other pulse sequences are also possible for thermometry, including CW spin resonance measurements without echos. The diamond is illuminated with the optical pulses of FIG. 3B and a microwave pulse sequence that includes a π/2 pulse, a first free precession time Δt, a 2π pulse, a second free precession time Δt, and another π/2 pulse. FIG. 11A is a wide-field image of fluorescence emitted by the NVs. FIGS. 10B and 10C are plots of normalized fluorescence versus the free precession time and the zero-field splitting detuning, respectively. Thermal echo sequences have applications in sensing the D parameter; that is, they can be used for thermometry, strain measurements, and pressure measurements.

Figures 12A, 12B:
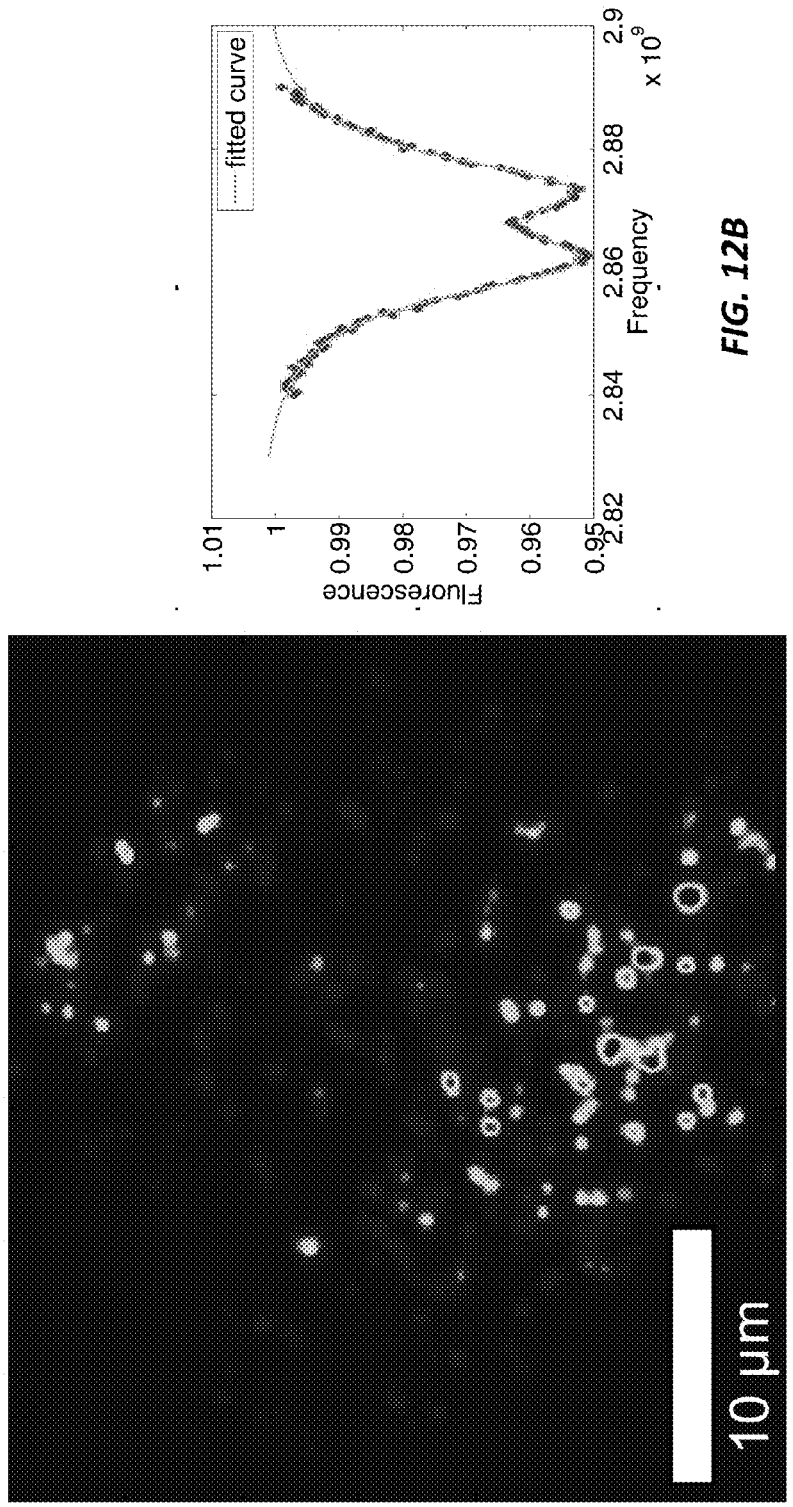
FIG. 12A is a fluorescence image of NV-containing nanodiamonds.
FIG. 12B is a pulsed optically detected magnetic resonance (ODMR) spectrum of a representative NV-containing nanodiamond.

FIG. 12A is a fluorescence image of NV-containing nanodiamonds. The individual nanodiamonds are about 100 nm in diameter. FIG. 12B is a pulsed optically detected magnetic resonance (ODMR) spectrum of a representative nanodiamond. It is spatially localized, but because there is not set NV axis, which can complicate alignment of the applied microwave field.

FIGS. 13A-13C illustrate $T_1$ excited state lifetime (relaxometry) measurements in high-pressure, high-temperature (HPHT) nanodiamonds with of a CVD diamond with a relatively high density of NVs (e.g., 100 ppm) and diameters of about 100 nm. The diamond is illuminated with the optical pulses of FIG. 3B separated by a decay time τ, but no microwave pulses. FIG. 13A is a wide-field image of fluorescence emitted by the NVs. FIG. 13B is a plot of the normalized fluorescence versus the decay time. FIG. 13C is a histogram of the number of fluorescence-emitting nanodiamonds versus measured excited state lifetime.

Figure 14C:
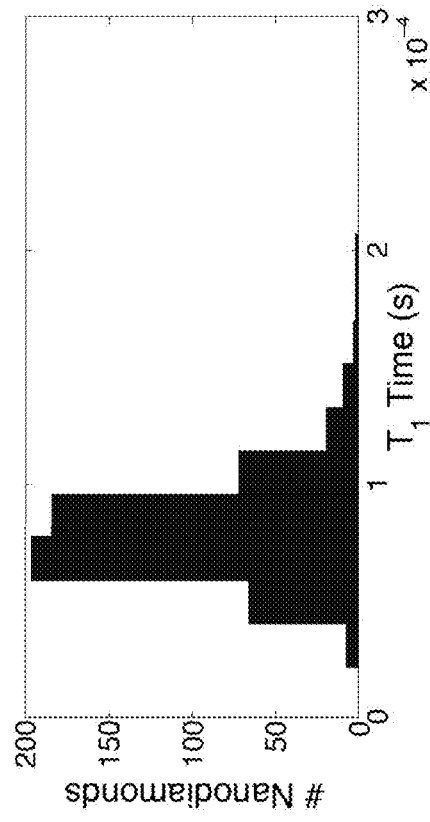
FIGS. 14A-14C illustrate $T_1$ excited state lifetime (relaxometry) measurements in HPHT nanodiamonds sputtered with silicon dioxide.
Figure 14B:
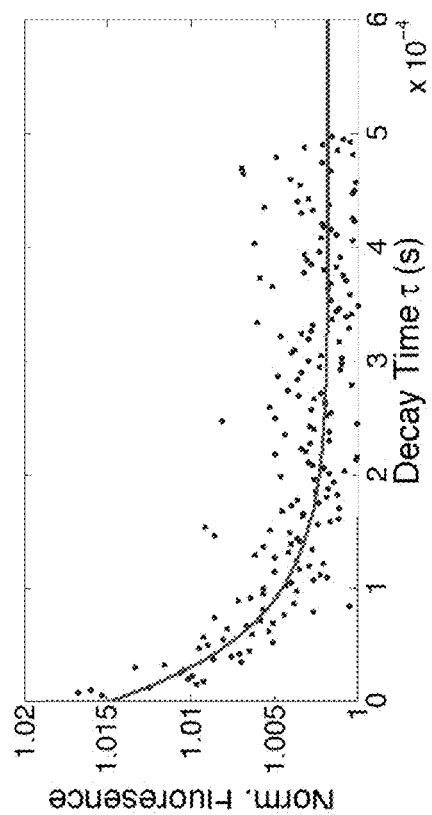
Figure 14A:
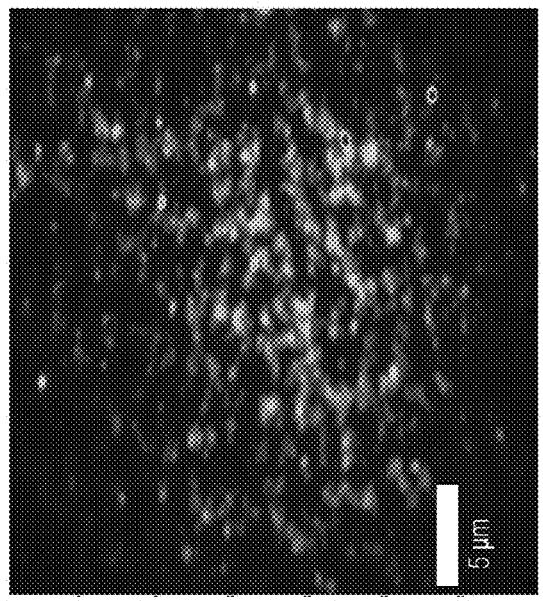

FIGS. 14A-14C illustrate $T_1$ excited state lifetime (relaxometry) measurements in the HPHT nanodiamonds of FIGS. 13A-13C sputtered with silicon dioxide. FIG. 14A is a wide-field image of fluorescence emitted by the NVs. FIG. 14B is a plot of the normalized fluorescence versus the decay time. And FIG. 14C is a histogram of the number of fluorescence-emitting nanodiamonds versus measured excited state lifetime. FIGS. 14B and 14C show a reduction in the excited-state lifetime, which suggests the presence of extra decay pathways.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of imaging at least one of an electric field, magnetic field, temperature, pressure, or strain applied to a color center, the method comprising:
   (A) applying a magnetic field from a microwave source to the color center so as to manipulate an electron spin state of the color center;
   (B) irradiating the color center with an optical pulse from a light source so as to excite the color center from a first energy level to a second energy level and to induce emission of fluorescence from the color center, the fluorescence representative of the at least one of the electric field, magnetic field, temperature, pressure, or strain applied to the color center; and
   (C) imaging, with a wide-field imaging system, the fluorescence emitted by the color center onto a detector array,
   wherein (C) comprises irradiating the color center with another optical pulse from the light source within a relaxation time associated with the second energy level.

2. The method of claim 1, further comprising, before (A):
   disposing the color center on a surface of an inorganic material; and
   exposing the inorganic material to the at least one of the electric field, magnetic field, temperature, pressure, or strain.

3. The method of claim 1, wherein the color center is disposed within a nanodiamond, and further comprising, before (A):
   functionalizing a surface of the nanodiamond; and
   disposing the nanodiamond within organic tissue.

4. The method of claim 1, wherein (A) comprises applying a plurality of microwave pulses to the color center in an absence of any other magnetic field.

5. The method of claim 1, wherein:
   the color center has a first orientation with respect to the magnetic field, and
   (A) further comprises manipulating an electron spin state of another color center, the other color center having a second orientation different than the first orientation with respect to the magnetic field.

6. The method of claim 1, wherein (C) comprises imaging fluorescence emitted by a plurality of color centers onto the detector array with the wide-field imaging system.

7. A system for imaging at least one of an electric field, magnetic field, temperature, pressure, or strain applied to a color center, the system comprising:
   a light source, in optical communication with the color center, to irradiate the first color center with an optical pulse so as to excite the color center from a first energy level to a second energy level and to induce emission of fluorescence from the color center, the fluorescence representative of the at least one of the electric field, magnetic field, temperature, pressure, or strain applied to the first color center;
   a microwave source, in electromagnetic communication with the color center, to apply a magnetic field to the color center so as to manipulate an electron spin state of the first color center; and
   a wide-field imaging system, in optical communication with the color center, to image the fluorescence emitted by the color center onto a detector array,
   wherein the microwave source is configured to apply the magnetic field at a first orientation with respect to the color center and at a second orientation with respect to another color center so as to manipulate the electron spin state of the color center and the electron spin state of the other color center.

8. A system for imaging at least one of an electric field, magnetic field, temperature, pressure, or strain applied to a plurality of color centers, the system comprising:
   a light source, in optical communication with the plurality of color centers, to irradiate the plurality of color centers with an optical pulse so as to excite the plurality of color centers from a first energy level to a second energy level and to induce emission of fluorescence from the plurality of color centers, the fluorescence representative of the at least one of the electric field, magnetic field, temperature, pressure, or strain applied to the plurality of color centers;
   a microwave source, in electromagnetic communication with the plurality of color centers, to apply a magnetic field to the plurality of color centers so as to manipulate an electron spin state of the plurality of color centers; and
   a wide-field imaging system, in optical communication with the plurality of color centers, to image the fluorescence emitted by the plurality of color centers onto a detector array,
   wherein the light source is configured to irradiate the plurality of color centers with another optical pulse within a relaxation time associated with the second energy level.

9. The system of claim 8, wherein the color center comprises a nitrogen vacancy.

10. The system of claim 8, wherein the color center is disposed on a surface of an inorganic material exposed to the at least one of the electric field, magnetic field, temperature, pressure, or strain applied to the color center.

11. The system of claim 8, wherein the color center is disposed within organic tissue exposed to the at least one of the electric field, magnetic field, temperature, pressure, or strain applied to the color center.

12. The system of claim 8, wherein the light source is configured to emit the optical pulse at a wavelength of about 532 nm.

13. The system of claim 8, wherein the microwave source is configured to apply a plurality of microwave pulses to the color center in an absence of any other magnetic field.

14. The system of claim 8, wherein the wide-field imaging system is configured to image fluorescence emitted by the color center onto the detector array.

15. A system for imaging at least one of an electric field, magnetic field, temperature, pressure, or strain applied to the color center applied to a nanodiamond, the system comprising:
   a laser, in optical communication with the nanodiamond, to illuminate the nanodiamond with an optical pulse so as to simultaneously to induce emission of fluorescence from a nitrogen vacancy in the nanodiamond and to excite the nitrogen vacancy in the nanodiamond from a first energy level to a second energy level;

a wide-field imaging system, in optical communication with the nanodiamond, to image the fluorescence emitted by the nitrogen vacancy to a point in an image plane; and a detector array, disposed within the image plane, to sense the fluorescence emitted by the nitrogen vacancy, wherein the laser is configured to illuminate the nanodiamond with another optical pulse within a relaxation time of the second energy level.

16. The system of claim 15, wherein the wide-field imaging system is configured to image fluorescence emitted by another nitrogen vacancy to the image plane.

17. The system of claim 15, further comprising:

a microwave source, in electromagnetic communication with the nanodiamond, to apply at least one microwave pulse to the nitrogen vacancy so as to manipulate an electron spin state of the first nitrogen vacancy.

18. A method of imaging at least one of an electric field, temperature, pressure, or strain applied to a color center, the method comprising:

(A) applying a plurality of microwave pulses from a microwave source to the color center in an absence of a magnetic field so as to manipulate an electron spin state of the color center;

(B) irradiating the color center with an optical pulse from a light source so as to excite the color center from a first energy level to a second energy level and to induce emission of fluorescence from the color center, the fluorescence representative of the at least one of the electric field, temperature, pressure, or strain applied to the color center; and (C) imaging, with a wide-field imaging system, the fluorescence emitted by the color center onto a detector array.

* * * * *

UNITED STATES PATENT AND TRADEMARK OFFICE
CERTIFICATE OF CORRECTION

PATENT NO. : 9,766,181 B2
APPLICATION NO. : 14/317534
DATED : September 19, 2017
INVENTOR(S) : Matthew Edwin Trusheim Page 1 of 1

It is certified that error appears in the above-identified patent and that said Letters Patent is hereby corrected as shown below:

On the Title Page

(60) Related U.S. Application Data, Column 1:
"Provisional application No. 61/840,852, filed on Jun. 28, 2013, provisional application No. 61/850,400"
Should read:
-- Provisional application No. 61/840,852, filed on Jun. 28, 2013, provisional application No. 61/860,400 --

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*